United States Patent [19]
Koiso et al.

[11] Patent Number: 5,975,074
[45] Date of Patent: Nov. 2, 1999

[54] SHEET TYPE HEATING ELEMENT AND METHOD OF MANUFACTURING THE SAME

[75] Inventors: Yasuhiko Koiso; Naoto Wagatsuma; Masayuki Fujisawa; Namoru Takahashi, all of Kanagawa, Japan

[73] Assignee: Japan Pionics Co., Ltd., Japan

[21] Appl. No.: 08/817,519

[22] PCT Filed: Oct. 13, 1995

[86] PCT No.: PCT/JP95/02108

§ 371 Date: Oct. 8, 1997

§ 102(e) Date: Oct. 8, 1997

[87] PCT Pub. No.: WO96/11654

PCT Pub. Date: Apr. 25, 1996

[30] Foreign Application Priority Data

Oct. 14, 1994 [JP] Japan .................................. 6-275824

[51] Int. Cl.$^6$ ...................................................... A61F 7/00
[52] U.S. Cl. .................... 126/204; 126/263.02; 604/291; 607/114
[58] Field of Search ......................... 126/263.02, 263.05, 126/263.07, 263.04, 206, 204; 604/291; 607/114, 96

[56] References Cited

U.S. PATENT DOCUMENTS 5,117,809   6/1992   Scaringe et al. .................... 126/263.07
5,163,504  11/1992   Resnick .............................. 126/263.07

FOREIGN PATENT DOCUMENTS

53-84246   7/1978   Japan .
63-37181   2/1988   Japan .
64-42018   2/1989   Japan .
2-142561   5/1990   Japan .
3-152894   6/1991   Japan .
7-59809    3/1995   Japan .
8-112303   5/1996   Japan .

*Primary Examiner*—James C. Yeung
*Attorney, Agent, or Firm*—Sterne, Kessler, Goldstein, & Fox, P.L.L.C.

[57] ABSTRACT

Water is adhered to the bottom face of a non-woven fabric having a large number of pores, then a heat generating powder composition is sprayed onto the top face of this fabric to be held in place. Another non-woven fabric is then superposed on the top face of the first non-woven fabric and the two non-woven fabrics are compressed. Water or a solution of electrolytes in water is then sprayed on the fabrics. Thereby, a sheet shaped heat generating body can be provided which uses a heat generating composition which generates heat when contacting air, which prevents concentration of the heat generating composition in one direction, and which is thin, flexible and has good heat generating properties.

20 Claims, 4 Drawing Sheets

SHEET TYPE HEATING ELEMENT AND METHOD OF MANUFACTURING THE SAME

BACKGROUND OF THE INVENTION

1. Field of the Invention

The present invention broadly relates to sheet shaped heat generating bodies, particularly to such thin and flexible heat generating sheets which reduce displacement and concentrate placement of heat generating composition, and the manufacturing method thereof

2. Related Art

Heat generators which have as their main component oxidizable metals such as iron powder are widely used as pocket heaters, wherein the heat generating composition which contacts with oxygen in the air to emit heat is packed in air permeable bags.

Although these kinds of heat generators are advantageous in that they may be used in a simple manner, they have problems in that when wearing the generator on the body, the heat generating composition moves down to the bottom of the bag due to its weight, not only during sports but also when standing still, so that the change of shape causes an uncomfortable feeling to the wearer and the heat generating feature becomes less effective.

Various efforts have been made to hold the heat generating composition in or between supporting members to form a sheet-like product as a means for reducing these defects. Described below are examples of such efforts:

a) A method of holding the heat generating composition with wire mesh or net shaped plastic objects (Patent Laid-Open Sho 53 (1978)-84246 Publication);

b) A method of superposing metal foils such as aluminum foils on non-woven fabric made of activated carbon fiber and impregnated with chloride, water or other oxidation auxiliary agents (Patent Laid-Open Sho 63 (1988)-37181 Publication);

c) A method of spraying a heat generating agent on Japanese paper impregnated with an oxidation auxiliary agent, and thereafter subjecting it to pressure to mold such product into a sheet-like shape (Utility Model Sho 64 (1989)-42018 Publication);

d) A method of laying one over the other a plurality of non-woven fabrics made of heat-fused fibers which may include plant fibers, and then distributing chemical heat generating agent therein (Patent Laid-Open Hei 2 (1990)-142561 Publication); and e) A method of distributing heat generating agent on a supporting sheet which comprises unevenly layered fibers with a large number of very fine pores, and to hold the agent thereon (Patent Laid-Open Hei 3 (1991)-152894 Publication).

Technical Problems to be Solved by the Invention

However, the related art described above has the following problems in the manufacturing process of the heat generating sheet or the resulting heat generator.

a) When holding the generator with wire mesh or net shaped plastic objects, the sheet-like product becomes more rigid and is impractical for use, and the heat generating composition powder becomes easily detached.

b) In products made by superposing metal foils such as aluminum foils on non-woven fabric made of activated carbon fibers, etc. impregnated with oxidation auxiliary agents, the metal surface area is considerably small in comparison to products using metal powders, such that a good heat generating effect cannot be achieved. If the number of foils is increased, this results in reducing the flexibility of the product.

c) In products made by spraying the heat generating agent on paper which is then subjected to pressure to form a sheet, the heat generating agent comes off through folding or shaking, which is not practical.

d) The combination of a plurality of non-woven fabrics by utilizing the water holding property of plant fibers and the heat fusion of synthetic fibers not only renders the structure and processing complicated, but also has practical problems in that the sheet-like object lacks flexibility due to instances where the non-woven fabrics do not adhere to each other, depending on the type and blending ratio of the heat fusive fibers and due to the rigid net-like structure in heat fusion.

e) Concerning the method of distributing heat generating compositions on the supporting sheet made of irregularly layered fibers with a large number of very fine pores, this is a good method in that the composition may be distributed and held inside the pores in a homogenous manner. However, due to the fact that after securing the iron powder, a suspension liquid containing activated carbon, etc. is sprayed, it is difficult to hold the heat generating composition as a whole in a homogenous mixture.

As shown above, it is strongly desired to develop a flexible heat generating body, wherein the heat generating sheet is manufactured so as to allow easy and homogenous distribution and holding of the heat generating composition while preventing leakage of the powder, and a method of manufacturing the same.

SUMMARY OF THE INVENTION

The inventors of the present invention have conducted research aimed at solving the problems described above with the goal of obtaining a thin, soft heat generating sheet with high heat generating capacity, wherein the heat generating composition is securely held without being displaced. The present invention achieves this goal by dampening the bottom face of a multi-poric, non-woven fabric with water and thereafter spraying a heat generating powder composition from the top face of said non-woven fabric and holding such powder.

In other words, the present invention is a heat generating sheet characterized in that after adhering water to the bottom face of a first non-woven fabric, a heat generating powder composition is sprayed on the top face of such fabric and held inside its pores. A second non-woven fabric is then superposed on the top face of the first non-woven fabric and compressed via a mold compressor to form a sheet product. The sheet product is then impregnated with water or a solution of electrolytes in water. Alternatively, the present invention is a heat generating sheet characterized in that water is adhered to the bottom face of a multi-poric, first non-woven fabric and/or the top face of a second non-woven fabric. The second non-woven fabric is then superposed on the bottom face of the first non-woven fabric. A heat generating powder composition is then sprayed onto the top face of the first non-woven fabric and held inside its pores. A third non-woven fabric is then superposed on the top face of the first non-woven fabric and is compressed via a mold compressor to form a sheet product. The sheet product is then impregnated with water or a solution of inorganic electrolytes in water. In a third embodiment of the present invention, a heat generating sheet is characterized in that a plurality of layers of non-woven fabric in a combination of non-woven fabrics are superposed via water adhesion or water adhesion plus compression, and at least one of said non-woven fabric layers holds a heat generating composition. The present invention also relates to a method of manufacturing each of the embodiments.

The present invention holds the heat generating composition with a first non-woven fabric by moistening the bottom face of the first non-woven fabric and spraying the heat generating powder composition from the top face, thereby causing homogeneous holding of the powder in the first non-woven fabric without leakage. Then, by superposing a second non-woven fabric thereon and compressing them, the non-woven fabrics do not separate, securing the fixing of the sheet shape, and providing a heat generating composition which is thin and flexible.

EMBODIMENTS OF THE INVENTION

The present invention may be applied to heat generators for warming the human body, warming animals and plants, heating and warming foods, and also heating and warming machines and equipment, etc., and the manufacturing method of such generators.

The non-woven fabric used in the present invention is a multi-poric, non-woven fabric, which has the property of being able to hold such heat generating composition material described below which is a material mixture used in powder form (hereinafter referred to as "powder composition") inside its pores, having great moisture holding capacity, and is mainly composed of plant fibers such as pulp, cotton and linen, or recycled fibers such as rayon. In addition, a mixture of plant fibers or recycled fibers with a slight amount of synthetic fibers such as nylon, polyester, acryl or polyolefin may be used, too. Among these materials, preferable is a non-woven fabric wherein the total sum of plant fibers and recycled fibers is 95% or more of the fiber content, because of their large moisture holding capacity and their ability to maintain the flexibility of the sheet without causing heat fusion when heating the product to compress and mold a sheet-shaped product. More preferably, the product utilizes a non-woven fabric which contains 98% or more of pulp, cotton, linen or rayon, etc.

There are no particular limits to the method of manufacturing the first non-woven fabric, which may be formed by an entanglement of fiber materials, or formed by using a small amount of adhesive agent or synthetic resin, etc. as binder. The greater the porosity rate of the first non-woven fabric, the easier the distribution of the powder composition into the pores, but as pores which are too large incur leakage of the powder, the porosity rate is normally 70–99.5%, preferably 80–99%.

The thickness of the first non-woven fabric is normally 0.5–25 mm depending upon the amount of heat generating composition to be held, and the porosity rate of the first non-woven fabric is preferably 1–10 mm. The measuring weight is normally 5–200 g/m$^2$, preferably 30–150 g/m$^2$.

In the present invention, the spraying of the composition material on the top face of the first non-woven fabric is conducted such that water is adhered to the bottom face of the first non-woven fabric, and then the composition material to sprayed thereon. By causing water to adhere to the bottom face of the first non-woven fabric, even large-pored, non-woven fabrics can hold powder without leakage due to the adhesion of water.

The amount of water to adhere to the bottom face of the first non-woven fabric need only be such so as to prevent leakage of powder composition from the bottom face of the first non-woven fabric by the moisture, which is normally 10–200 g/m$^2$ depending upon the measuring weight, thickness and material quality, etc. of the first non-woven fabric, and preferably 20–120 g/m$^2$.

The water adhesion method need only be such so as to enable adjustment of the amount of the adhering water and a homogenous adhesion, for example the method of atomizing or sticking water with a roll on the bottom face of the first non-woven fabric.

In the present invention, the material composing the powder composition is, for example, oxidizable metal powder, activated carbon, water-holding agent.

Concerning the inorganic electrolytes, they are one component of the powder composition if mixed as solid body into the materials above, and if sprayed and impregnated in the form of aqueous solution after the molding of the sheet, for example, they are not included into the powder composition.

The oxidizable metal powder is iron powder and aluminum powder, etc., but normally, iron powder is used, namely reduced iron powder, atomized iron powder, electrolytic powder, etc.

Activated carbon is used as the reactive agent and also as the water holding agent, and is normally palm activated carbon, wood flour carbon, or peat carbon, etc.

The inorganic electrolytes used are preferably chlorides of alkali metals, alkali earth metals and heavy metals, and sulfates of alkali metals, for example sodium chloride, potassium chloride, calcium chloride, magnesium chloride, ferric chloride, sodium sulfate, etc.

The water holding agent is pearlite powder, vermiculite, macromoleculic water holding agent, etc., but is preferably a macromoleculic water holding agent.

The particle size of the powder composition is normally not more than 60 mesh, preferably containing at least 50% of particles which are not larger than 100 mesh.

The heat generating composition is made by adding and mixing water or a solution of inorganic electrolytes in water to the powder composition described above. The blending ratio in the whole of the heat generating composition cannot be specified in general, as it depends upon the properties and shape of the non-woven fabric, and the heat generating function to be achieved. As an example, when setting the oxidizable metal powder as 100 parts by weight, the activated carbon may be 5–20 parts by weight, the inorganic electrolytes 1.5–10 parts by weight, and water 25–60 parts by weight.

In addition, it is also possible to mix water holding agents such as pearlite powder, vermiculite or macromoleculic water holding agent, or hydrogen generation depressor or consolidation preventor, as desired.

Among those described above, the water, or the water and inorganic electrolytes will be supplied after the molding into a sheet shape.

Examples of the method of holding the heat generating composition inside the pores of the first non-woven fabric are as follows: a) spraying the mixture of powder material such as iron powder, activated carbon, inorganic electrolytes and the like on the first non-woven fabric, then subjecting the fabric to vibration to cause the mixture to proceed inside the pores to be held therein; or b) spraying the mixture of powder materials with exception of the inorganic electrolytes such as iron metals and activated carbon onto the top of the first non-woven fabric, subjecting the fabric to vibration to cause the mixture to proceed inside the pores to be held therein, then, after the molding to a sheet shape, spraying such inorganic electrolytes as a solution in salt water. In both cases a) and b), the alternative to subjecting the fabric to vibration is to subject the first non-woven fabric to suction from the bottom direction, thereby causing distribution and holding of the powder.

Among these two, method b) is preferable in that the inorganic electrolytes can be distributed on the whole surface in a homogenous manner.

As stated above, by causing water to stick to the bottom face of the first non-woven fabric and spraying and holding the powder composition, the composition material itself is secured by the adhesion of water to the wet bottom face of the first non-woven fabric, so that the distribution of powder composition tends to increase from the bottom face of the first non-woven fabric to its top face.

The amount of heat generating composition to be held inside the first non-woven fabric depends upon the thickness of the first non-woven fabric, the final thickness of the heat generator and the desired heat generating effects, etc., but is normally 150–10,000 $g/m^2$ of supportive body, and preferably 1,000–5,000 $g/m^2$.

If the held amount is less than 150 g, the generated heat temperature and duration of the generated heat are reduced, but when the held amount exceeds 10,000 g, the heat generator becomes thicker, so that the molding of a thin and flexible sheet becomes difficult.

The second non-woven fabric functions to hold the powder composition remaining on the top face of the first non-woven fabric and to prevent leakage of the powder composition from the top face, so that preferably, it has a large water holding capacity and has no heat-fusion property, so that it is a non-woven fabric made of the same material as that of the first non-woven fabric, namely pulp, cotton, linen or rayon, etc.

It is desirable for the porosity rate of the second non-woven fabric to be slightly smaller than that of the first non-woven fabric, normally 60–99%, and preferably 70–98%. Otherwise, if the porosity rate is too large, the powder is likely to leak.

The thickness of second non-woven fabric depends upon its porosity rate and the amount of powder composition held. Its thickness is normally 0.1–10 mm, preferably 0.5–5 mm. Its weight is normally 5–150 $g/m^2$, and preferably 20–100 $g/m^2$.

In the present invention, the layered product containing the first non-woven fabric which holds the powder composition and the second non-woven fabric is compressed by a compressor and processed into the shape of a sheet. The compression may be conducted by utilizing a pressing machine or pressing roll on the layered product. The compression may be conducted by using a plane or flat roll, but in order to prevent separation of the compressed sheet in the non-woven fabrics, it is preferable to form protrusions in the shape of waves, turtlebacks, rings, polka dots, stitch designs or others to form an embossed face.

The compressing may be conducted under heating. Heat compressing is advantageous in that the moisture heating secures the fixing of the shape even more.

The compression temperature and pressure depend upon the material qualities of the first and second non-woven fabrics and the amount of powder composition to be held, which cannot be specified in general. As an example, when using a heating roll with embossed face, the temperature normally ranges from ordinary temperature up to 300° C., and the linear pressure from around 0.5 through 300 kg/cm. In this way, the shape of the load is secured in the compressed state, forming a thin sheet.

The thickness of the heat generating sheet will be selected according to the heat generation to be achieved and the use, but in order to utilize the properties as a sheet to design them as thin as possible, they are normally 6 mm or less, preferably 4 mm or less. Concerning the size, the sheet will be cut in appropriate sizes according to the purpose of use.

Water is supplied to the sheet product through atomization or roll adhesion. This includes the amount of the water or the solution of inorganic electrolytes in water with which the sheet product is either to be impregnated as one component of the heat generator, or the total amount of water and inorganic electrolytes.

The sheet-like heat generator described above is stored in this state, or, in order to obtain those heat generating properties corresponding to its use, in a bag made of laminated film of polyethylene having permeable pores and non-woven fabric, or a bag made of a permeable film with micropores, then sealed in a non-permeable bag for storage, to be used as pocket heaters or medical heat generating bags.

In addition, the bag may also be used for warming animals and plants, heating and warming foods, and heating and warming machines and equipment, etc.

In the present invention, when holding the powder composition in the first non-woven fabric, it is possible to superpose a fine, third non-woven fabric on the bottom face of the first non-woven fabric to prevent powder from falling out of the first non-woven fabric even when its pores are large.

The third non-woven fabric may be composed mainly of materials such as of pulp, cotton, linen, rayon and other fibers, namely non-woven fabric made of pulp, cotton, linen, or rayon, etc. and paper-like products such as tissue paper.

The weight of the third non-woven fabric is normally 5–150 $g/m^2$, and preferably 10–100 $m^2$.

When superposing the third non-woven fabric on the bottom face of the first non-woven fabric, water maybe applied to the bottom face of the first non-woven fabric and/or the top face of the third non-woven fabric and then superposed. By thus superposing the first and third non-woven fabrics in a moist state, they are superposed in a close manner through their moisture adhesion, requiring no adhesive agent, which is a great advantage.

The amount of water to be applied to the non-woven fabric is normally 10–200 $g/m^2$, preferably 20–150 $g/m^2$.

In the present invention, when superposing the second non-woven fabric on the top face of the first non-woven fabric, water may first be adhered to the bottom face of the second non-woven fabric, and thereafter be superposed. The method of adhering water to the second non-woven fabric may be water atomizing or roll adhesion, and the applied amount is normally 15–300 g/m², preferably 30–200 g/m².

Instead of adhering water to the bottom face of the second non-woven fabric, it may be adhered to the top face of the first non-woven fabric, or on both non-woven fabrics. When adhering water to the top face of the first non-woven fabric, a portion of the powder composition may scatter when using certain adhesion methods, so that the method of adhesion to the second non-woven fabric is preferable.

When superposing first and second non-woven fabrics with the appliance of water, the fabrics are superposed closely onto each other due to wetness adhesion, which not only prevents the heat generating powder composition material from scattering, but also allows smooth introduction into the compressor, and when using a heating compressor, the moist heating effect allows a secure fixing of the shape, which are great advantages.

According to the present invention, the sheet made of first and second non-woven fabrics, and the sheet made of first, second, and third non-woven fabrics are sheet products superposed through water adhesion and compression adhesion.

By superposing a plurality of these heat generating sheets, a product may be made by superposing a plurality of layers of heat generating sheets. During the manufacture process of the sheet product, it is also possible to stack the non-woven fabrics as third-first-second-first-second from the bottom, or as third-first-first-first-second from the bottom, and cause the powder composition to be mainly held within the first non-woven fabric.

By superposing a plurality of layers as described above, the thickness of the heat generator may be determined arbitrarily. The plurality of layers are superposed by water adhesion, or water adhesion plus compression adhesion, while at least one of such layers is a heat generator holding heat generating powder composition, which avoids a strong three-dimensional wired structure, so that it is an effective flexible heat generator.

PREFERRED EMBODIMENTS

Now, the present invention will be exemplified with reference to the drawings, and explained more specifically. It is understood that the specific embodiments are for illustrative purpose and the present invention is not limited such embodiments.

Figure 1:
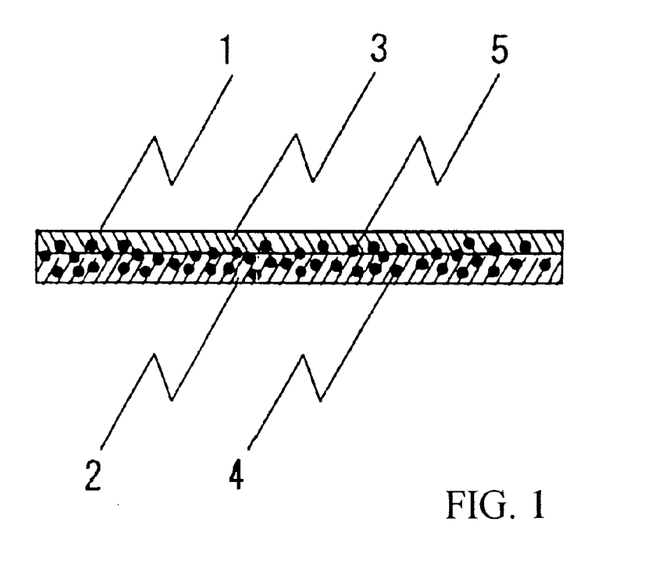
FIG. 1 is a cross sectional view of heat generating sheet 1.

FIG. 1 is a cross sectional view of a heat generating sheet 1 according to the present invention.

Figure 2:
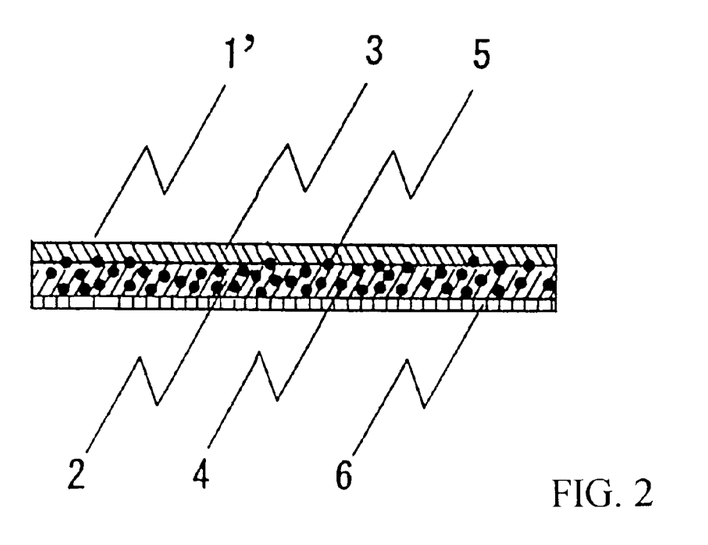
FIG. 2 is a cross sectional view of heat generating sheet 1'.

FIG. 2 is a cross sectional view of a heat generating sheet 1' carried out in a different mode from that of FIG. 1. In both FIGS. 1 and 2, reference numeral 2 indicates a first non-woven fabric, reference numeral 3 indicates a second non-woven fabric. Reference numeral 4 indicates a heat generating composition held in first non-woven fabric 2. Reference numeral 5 indicates the heat generating composition held in non-woven fabric 3. Reference numeral 6 indicates a third non-woven fabric.

Figure 3:
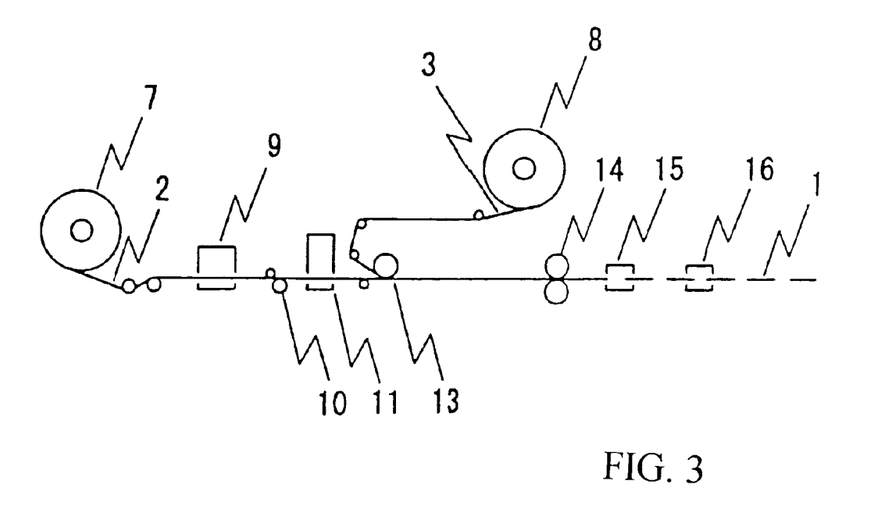
FIG. 3 discloses the first example for performing the steps of the present invention.

FIG. 3 discloses a first example for performing the steps of the present invention. In FIG. 3, a roll 7 of first non-woven fabric 2 is provided for use with the present invention. Water is applied to first non-woven fabric 2 on its bottom face by a water atomizer 9. First non-woven fabric 2 is then subjected to roll 10, sprayed with the powder composition at powder filler 11, and then subjected to vibration to hold the heat generating composition inside the pores of first non-woven fabric 2.

Then, second non-woven fabric 3, supplied by a roll 8, is superposed via a roller 13, heat compressed at a compressor 14, cut into the desired size by a cutter 15, and then sprayed with a solution of inorganic electrolytes in water at salt water sprayer 16 to finally form heat generating sheet 1.

Figure 4:
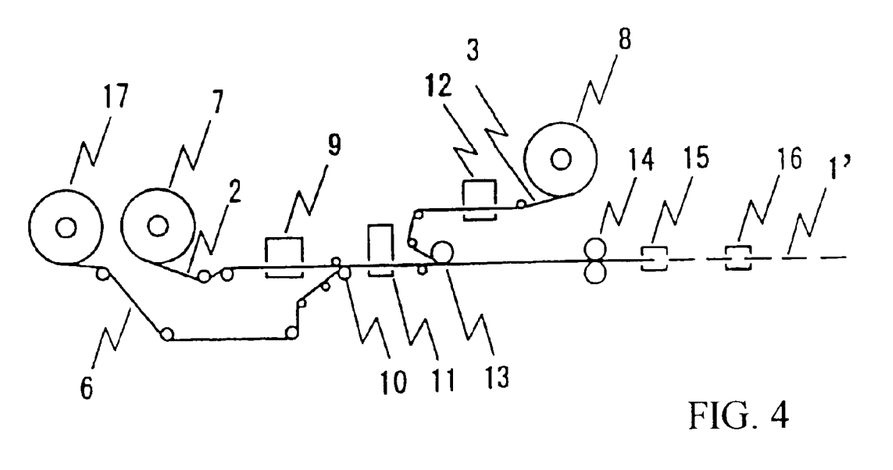
FIG. 4 discloses the second example for performing the steps of the present invention.
Figure 5:
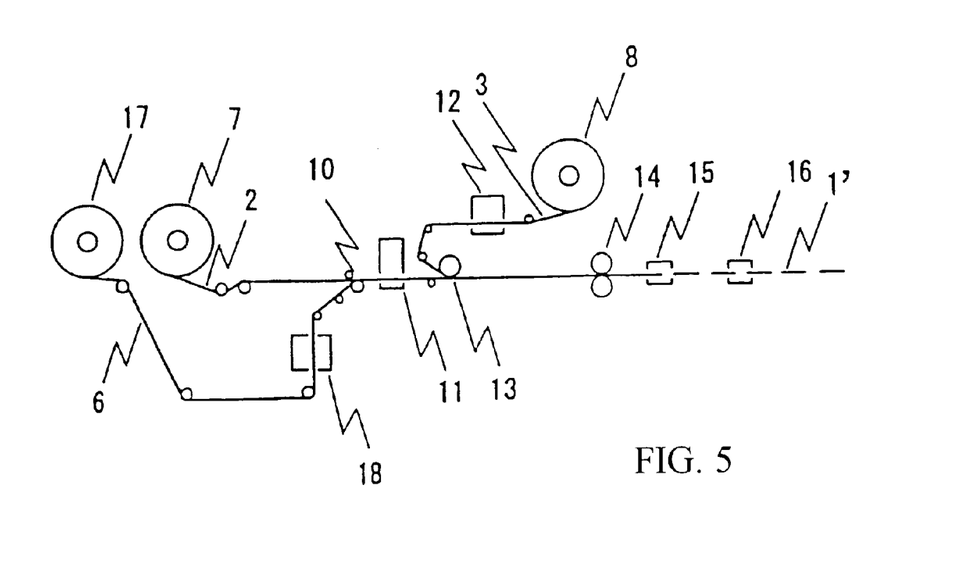
FIG. 5 discloses the third example for performing the steps of the present invention.

FIGS. 4 and 5 illustrate second and third examples for performing the steps of the present invention when superposing non-woven fabric 6 on a bottom face of first non-woven fabric 2.

The heat generating sheet obtained as above is packed in bags with adjusted permeability in accordance with their use, and used as pocket heaters or medical equipment by successively utilizing the method of sealing such sheet in non-permeable bags.

Figure 7:
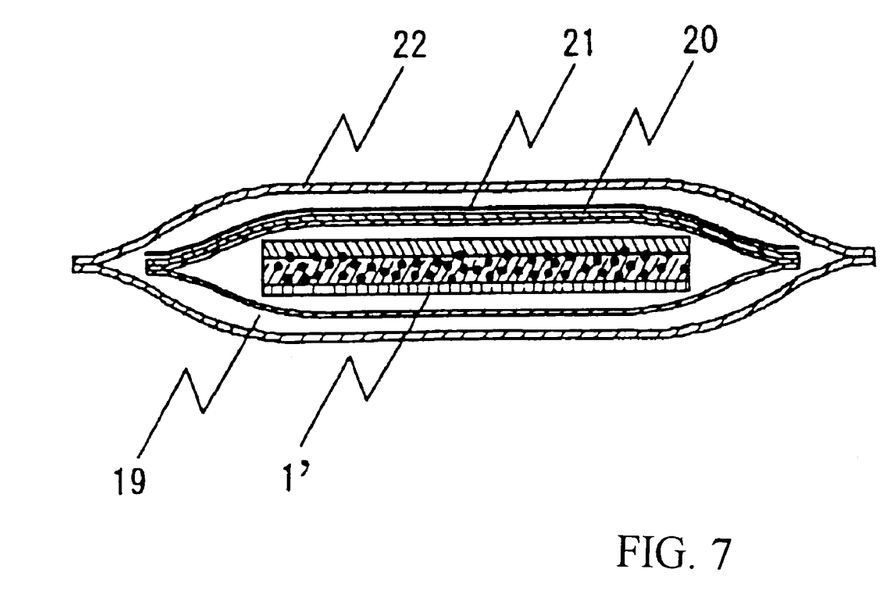
FIG. 7 is a cross sectional view of a plaster-type, sheet-shaped pocket heater.

FIG. 7 is a cross sectional view of a plaster-type pocket heater using a heat generator sheet according to the present invention. Reference numeral 19 indicates an inner bag, reference numeral 20 a layer of adhesive agent, reference numeral 21 separating paper, and reference numeral 22 an outer bag.

Embodiment 1

In the device shown in FIG. 3, first non-woven fabric 2, approximately 1.9 mm thick, weighing approximately 57 g/m² and with an approximate porosity rate of 97.9%, made of wooden pulp (Habix K. K.; "J Soft") was sent with 12.3 m/min speed. Water was homogeneously atomized on a bottom face of first non-woven fabric 2 at a rate of 35 g/m². Then, a mixture of 90% iron powder, 8% activated carbon, 2% macromoleculic water holding agent was sprayed from a top face of first non-woven fabric 2 at a rate of 1,100 g/m², and at the same time, first non-woven fabric 2 was shaken up and down to hold such mixture in its pores. Thereafter, second non-woven fabric 3, made of wooden pulp with thickness of 1.1 mm, weighing 40 g/m², and a porosity rate of 97.6% (Honshu Selshi K. K., "Kinokurosu") was superposed on the top face of first non-woven fabric 2, and the sheet was put through a heat compressing roller to form the shape of a sheet. The heat compressing roller was embossed face with striped design on the roller face, and set at 195° C., with linear pressure of 40 kg/cm.

Then, the sheet product was cut in the size of 8.5 cm×12.5 cm. Thereafter, a salt water solution which is a mixture of 8.5% sodium chloride and 91.5% water was sprayed at the rate of 520 g/m² to obtain an approximately 2 mm thick heat generating sheet. This heat generator is flexible and the heat generating composition is held in place. This heat generator was stored in a flat shaped inner bag, of which one face is composed of a multi-layered sheet with a microporic film made of polypropylene with 350 g/m² day moisture permeability and a nylon non-woven fabric, and of which the other face is composed of a laminated film of polyethylene film and nylon non-woven fabric to form the heat generating sheet. This was further sealed in a non-permeable bag, then stored.

Figure 6:
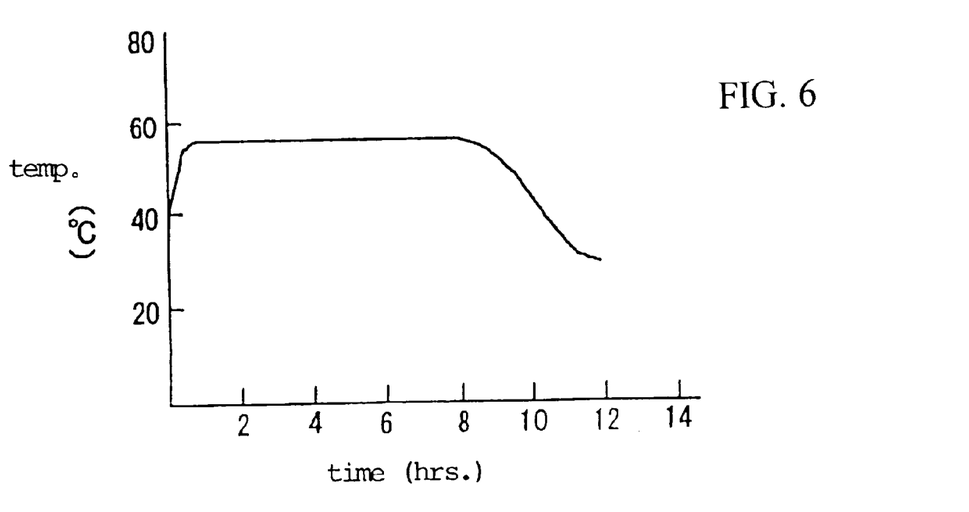
FIG. 6 is a diagram showing the heat generative properties of the present invention.

After two days, the heat generating sheet was taken out of the outer bag and indoor measurements were conducted concerning the heat-generating effect based on the JIS S-4100 heat generation test method at room temperature 20° C. and relative humidity 65%. As a result, the heat generating effect shown in FIG. 6 was obtained.

The temperature exceeded 40° C. after 8.5 minutes, and reached 52° C. in 70 minutes. The duration of heat generation for 40° C. or more was approximately 10 hours.

Furthermore, when taking this heat generating sheet out of the outer bag and wearing it on the body, a comfortable temperature could be obtained for around 12 hours, while always maintaining a flexible sheet shape.

Embodiment 2

In the device shown in FIG. 4, first non-woven fabric 2 made of wooden pulp (Habix K. K.; "J Soft"), approximately 1.9 mm thick, weighing approximately 57 g/m² and with an approximate porosity rate of 97.9%, was sent with 12.3 m/min speed, and water was homogeneously atomized on the bottom face of first non-woven fabric 2 at a rate of 40 g/m². Then, after superposing a tissue paper of 30 g/m² measuring weight on the bottom face of first non-woven fabric 2, a mixture of 90% iron powder, 8% activated carbon, 2% macromoleculic water holding agent was sprayed from the top face of first non-woven fabric 2 at a rate of 1,100 g/m², and at the same time, the non-woven fabric was shaken up and down to hold such mixture in its pores. Thereafter, an the top face of first non-woven fabric 2, second non-woven fabric 3 made of wooden pulp, 1.1 mm thick, weighing 40 g/m², and with a porosity rate of 97.6% (Honshu Seishi K. K.; "Kinokurosu") was superposed after having water adhered to its bottom face at the rate of 60 g/m².

Thereafter, the heat generating sheet was obtained in the same way as in Embodiment 1.

This heat generator is flexible and there was no falling of the heat generating composition. This heat generating sheet was stored in a flat inner bag, of which one face is a multi-layered sheet of microporic propylene film with a moisture permeability of 350 g/m² day and a nylon non-woven fabric, and of which the other face is a laminated film of polyethylene and nylon non-woven fabric to form a sheet-shaped heat generating bag. This bag was further sealed in a non-permeable outer bag.

After two days, the heat generating sheet was taken out from the outer bag and measurements made with regard to its heat generating effect in the same way as in Embodiment 1. As a result, the temperature exceeded 40° C. after 9 minutes, and reached 52° C. in 65 minutes. The duration of heat generation of 40° C. or more was approximately 11 hours.

Furthermore, when this heat generating sheet was taken out of the outer bag and worn on the body, a comfortable temperature could be obtained for around 12 hours, while always maintaining a flexible sheet shape.

Embodiment 3

Using the device shown in FIG. 5, the water atomization on the bottom face of first non-woven fabric 2 ("J Soft") was replaced with the following: 30 g/m² water was atomized on the top face of a tissue paper with measuring weight 30 g/m² to moisten the paper, which was then superposed on the bottom face of first non-woven fabric 2 ("J Soft") to obtain the heat generating sheet in the same way as in Embodiment 2.

This heat generator was flexible and allowed no falling of the heat generating composition.

Embodiment 4

Using the device shown in FIG. 4, first non-woven fabric 2 made of wooden pulp, approximately 1.2 mm thick and weighing 40 g/m² (Honshu Seishi K. K.; "Kinokurosu") was sent with 12.3 m/min speed, and water was homogeneously atomized on the bottom face of first non-woven fabric 2 at a rate of 40 g/m². Then, after superposing a tissue paper of 27 g/m² measuring weight on the bottom face of first non-woven fabric 2, a mixture of 90% iron powder, 8% activated carbon, 2% macromoleculic water holding agent was sprayed from the top face of first non-woven fabric 2 at a rate of 1,430 g/m², and at the same time, first non-woven fabric 2 was shaken up and down to hold such mixture in its pores. Thereafter, on the top face of first non-woven fabric 2, second non-woven fabric 3 made of wooden pulp, 1.5 mm thick and weighing 60 g/m² (Honshu Seishi K. K., "Kinokurosu") was superposed after having water adhered to its bottom face at the rate of 60 g/m². This sheet was put through a heat compressing roller with an embossed face with striped design on the roller face and set at 200° C., linear pressure 166 kg/cm to form the shape of a sheet.

In order to measure the flexibility of this sheet, a test piece 25 mm wide and 88 mm long was cut therefrom, and, using the Galle method set forth in JIS L-1096 and a bending repulsion test unit, the bending repulsion of this sheet was measured.

Also, salt water which is a mixture of 8.5% sodium chloride and 91.5% water was sprayed on the sheet at the rate of 608 g/m², then a test piece was immediately cut therefrom and the bending repulsion measured. As a result, the bending repulsion before spraying of the salt water was 1217 mgf, and that after the spraying of the salt water was 1450 mgf Thereafter, the heat generating sheet was obtained in the same way as in Embodiment 1 with the exception that the salt water to be sprayed was 608 g/m².

This heat generator is flexible and there was no falling out of the heat generating composition. This heat generating sheet was stored in a flat inner bag, of which one face was composed of a multi-layered sheet of microporic film made of polypropylene with a moisture permeability of 350 g/m² day and a nylon non-woven fabric, and of which the other face was composed of a laminated film of polyethylene and nylon non-woven fabric with an additional layer of adhesive agent and separation paper superposed thereon to form a sheet-shaped heat generating bag. This bag was further sealed in a non-permeable outer bag.

After two days, the heat generating sheet was taken out from the outer bag and measurements made with regard to its heat generative effect in the same way as in Embodiment 1. As a result, the temperature exceeded 40° C. after 8 minutes, and reached 52° C. in 65 minutes. The duration of heat generation for 40° C. or more was approximately 12 hours.

Furthermore, when this heat generating sheet was taken out of the outer bag and worn on the body, a comfortable temperature could be obtained for around 12 hours, while always maintaining a flexible sheet shape.

Comparative Example 1

In the device shown in FIG. 4, first non-woven fabric 2, approximately 2.5 mm thick, weighing 38 g/m², with a 98.7% porosity rate, made of 50% polyester and 50% heat fusion polyester (Marusan Sangyo K. K. "Estermelty") was sent with 12.3 m/min speed, and water was homogeneously atomized on the bottom face of first non-woven fabric 2 at a rate of 40 g/m². Then, after superposing tissue paper weighing 27 g/m² on the bottom face of first non-woven fabric 2, a mixture of 90% iron powder, 8% activated carbon, and 2% macromoleculic water holding agent was sprayed from the top-face of the non-woven fabric at a rate of 1,430 g/m². At the same time, first non-woven fabric 2 was shaken up and down to hold such mixture in its pores. Thereafter, on the top face of first non-woven fabric 2, second non-woven fabric 3, made of wooden pulp 1.5 mm thick and weighing (Honshu Seishi K. K.; "Kinokurosu") was superposed after having water adhered thereto at its bottom face at the rate of 60 g/m². This sheet was put through a heat compressing roller with an embossed face with striped design an the roller face, and set at 200° C. and linear pressure 166 kg/cm to form the shape of a sheet.

The same flexibility test as with Embodiment 4 was carried out for this sheet. As a result, the bending repulsion before spraying of the salt water was 2647 mgf, and that after the spraying of the salt water was 2267 mgf Thereafter, the heat generating sheet was obtained in the same way as in Embodiment 4.

This heat generator did not show any falling out of the heat generating composition, but was hard compared to the heat generating sheet of Embodiment 4 and flexibility was low.

This heat generating sheet was stored in a flat inner bag, of which one face was composed of a multi-layered sheet of microporic propylene film with a moisture permeability of 350 g/m² day and a nylon non-woven fabric, and of which the other face was composed of a laminated film of polyethylene and nylon non-woven fabric with an additional layer of adhesive agent and separation paper superposed thereon to form a sheet-shaped heat generating bag. This bag was further sealed in a non-permeable outer bag.

After two days, the heat generating sheet was taken out of the outer bag and continued to hold a comfortable temperature when worn on the body and maintained the sheet shape, but was always hard, causing an uncomfortable feeling.

What is claimed is:

1. A sheet shaped heat generating body comprising a sheet product impregnated with water or a solution of inorganic electrolytes in water, said sheet product including:
    a porous, first non-woven fabric with water adhered to a bottom face of said first non-woven fabric;
    a heat generating powder composition sprayed on a top face of said first non-woven fabric to be held inside pores of said first non-woven fabric; and
    a second non-woven fabric superposed on said top face of said first non-woven fabric,
    wherein said first non-woven fabric and said second non-woven fabric are compressed via a mold compressor to form the sheet product.

2. A sheet shaped heat generating body comprising a sheet product impregnated with water or a solution of inorganic electrolytes in water, wherein said sheet product comprises:
    a first non-woven fabric;
    a third non-woven fabric superposed on a bottom face of said first non-woven fabric;
    a second non-woven fabric superposed on a top face of said first non-woven fabric; and
    a heat generating powder composition sprayed from the top face of said first non-woven fabric to be held inside pores of said first non-woven fabric;
    wherein the bottom face of said first non-woven fabric and the top face of said third non-woven fabric are bonded by water adhesion, and
    said second non-woven fabric and said first non-woven fabric are compressed via a mold compressor to form the sheet product.

3. A sheet shaped heat generating body comprising a plurality of non-woven fabrics mutually superposed via water adhesion or water adhesion plus compression, wherein at least one of said non-woven fabrics holds a heat generating composition inside its pores.

4. A sheet shaped heat generating body according to claim 1 or 2, wherein said first non-woven fabric has as its main component fibers selected from pulp, cotton, linen and rayon, and wherein said first non-woven fabric has a porosity rate of 60–99.5%, is 0.5–25 mm thick, and weighs 5–200 g/m².

5. A sheet shaped heat generating body according to claim 1, wherein said second non-woven fabric has as its main component fibers selected from pulp, cotton, linen and rayon, and wherein said second non-woven fabric weighs 5–150 g/m².

6. A sheet shaped heat generating body according to any one of claims 2 through 5, wherein said heat generating powder composition has as its main components iron powder and activated carbon, or iron powder, activated carbon and inorganic electrolytes, etc. and includes a solid component which contacts with the oxygen in air to generate heat.

7. A sheet shaped heat generating body according to any one of claims 1 and 2, wherein said first and second non-woven fabrics are superposed by adhering water on the top face of said first non-woven fabric and/or a bottom face of said second non-woven fabric.

8. A sheet shaped heat generating body according to claim 5, wherein the amount of water adhered to said bottom face of said first non-woven fabric is 10–200 g/m².

9. A sheet shaped heat generating body according to any one of claims 1 through 3, wherein said non-woven fabrics include a joggle face formed from an embossed face of said mold compressor.

10. A method of manufacturing a sheet shaped heat generating body, comprising the steps of:
    adhering water to a bottom face of a porous, first non-woven fabric;
    spraying a heat generating powder composition on a top face of said first non-woven fabric, wherein said heat generation powder composition is held inside pores of said first non-woven fabric;
    superposing a second non-woven fabric on said top face of said first non-woven fabric and subsequently compressing said first non-woven fabric and said second non-woven fabric via a mold compressor to form a sheet product; and
    impregnating said sheet product with water or a solution of inorganic electrolytes in water.

11. A method of manufacturing a sheet shaped heat generating body, comprising the steps of:
    adhering water to a bottom face of a porous, first non-woven fabric and/or a top face of a third non-woven fabric;
    superposing said third non-woven fabric on said bottom face of said first non-woven fabric;
    spraying a heat generating powder composition on a top face of said first non-woven fabric, wherein said heat generating powder is held inside pores of said first non-woven fabric;
    superposing a second non-woven fabric on said top face of said first non-woven fabric and subsequently compressing said first non-woven fabric and said second non-woven fabric via a mold compressor to form a sheet product; and
    impregnating said sheet product with water or a solution of inorganic electrolytes in water.

12. A method of manufacturing a sheet shaped heat generating body, comprising the steps of:

superposing a plurality of layers of a first non-woven fabric and a second non-woven fabric or of a first non-woven fabric, a second non-woven fabric and a third non-woven fabric via water adhesion or water adhesion plus compression, and causing a heat generating powder to be held in pores of at least one of said non-woven fabrics.

13. A method of manufacturing a sheet shaped heat generating body according to any one of claims 10 through 12, wherein said first non-woven fabric has as its main component fibers chosen from pulp, cotton, linen and rayon, and wherein said first non-woven fabric has a porosity rate of 60–99.5%, is 0.5–25 mm thick, and weighs 5–200 g/m$^2$.

14. A method of manufacturing a sheet shaped heat generating body according to claim 10, wherein said second non-woven fabric has as its main component fibers selected from pulp, cotton, linen and rayon, and wherein said second non-woven fabric weighs 5–150 g/m$^2$.

15. A method of manufacturing a sheet shaped heat generating body according to any one of claims 10 through 12, wherein said heat generating powder composition has as its main component iron powder and activated carbon, or iron powder, activated carbon and inorganic electrolytes, and includes a solid component which generates heat when said solid component comes into contact with oxygen in air.

16. A method of manufacturing a sheet shaped heat generating body according to any one of claims 10 through 12, wherein said first and second non-woven fabrics are superposed by adhering water to said top face of said first non-woven fabric and/or a bottom face of said second non-woven fabric.

17. A method of manufacturing a sheet shaped heat generating body according to claim 16, wherein the amount of water adhered to said bottom face of said first non-woven fabric and/or said top face of said second non-woven fabric is 10–200 g/m$^2$.

18. A method of manufacturing a sheet shaped heat generating body according to any one of claims 10 through 12, wherein said mold compressor has embossing on at least one of its compressing faces.

19. A sheet shaped heat generating body according to claim 2, wherein at least one of said second and third non-woven fabrics has as its main component fibers selected from pulp, cotton, linen and rayon, and wherein said second non-woven fabric weighs 5–150 g/m$^2$.

20. A method of manufacturing a sheet shaped heat generating body according to any one of claims 11 and 12, wherein at least one of said second and third non-woven fabrics has as its main component fibers selected from pulp, cotton, linen and rayon, and wherein said second non-woven fabric weighs 5–150 g/m$^2$.

* * * * *